United States Patent [19]

Dekeyser et al.

[11] Patent Number: 5,872,121
[45] Date of Patent: Feb. 16, 1999

[54] PESTICIDAL HYDRAZIDE DERIVATIVES

[75] Inventors: Mark Achiel Dekeyser, Waterloo, Canada; Paul Thomas McDonald, Middlebury, Conn.

[73] Assignee: Uniroyal Chemical Company, Inc., Middlebury, Conn.

[21] Appl. No.: 915,762

[22] Filed: Aug. 21, 1997

Related U.S. Application Data

[62] Division of Ser. No. 614,291, Mar. 12, 1996, Pat. No. 5,700,831.

[51] Int. Cl.$^6$ .......................... A01N 43/10; A01N 43/40; C07D 213/56; C07D 333/38
[52] U.S. Cl. .......................... 514/256; 514/355; 514/365; 514/446; 514/471; 544/335; 546/315; 548/200; 549/22; 549/487
[58] Field of Search ........................... 544/335; 546/315; 548/200; 549/72, 487; 514/256, 355, 365, 446, 471

[56] References Cited

U.S. PATENT DOCUMENTS 3,897,494  7/1975  Alexiev ................................. 260/561

FOREIGN PATENT DOCUMENTS 0234944  9/1987  European Pat. Off. .
0527112  2/1993  European Pat. Off. .

OTHER PUBLICATIONS

Dilkman et al, "N,N–Bis(2–chloroethyl)hydraides of carboxylic acids as potential antineoplastic substances", Chemical Abstracts No. 61807, vol. 75, No. 9 (1971).

Zakhariev et al., Chemical Abstracts, vol. 112, abstract 199003, 1990.

Raikova et al., Chemical Abstracts, vol. 98, abstract 172717, 1983.

Raikova et al., Chemical Abstracts, vol. 95, abstract 35175, 1981.

Dauvarte et al., Chemical Abstracts, vol. 78, abstract 92412, 1973.

Ivin et al., Chemical Abstracts, vol. 75, abstract 35924, 1971.

*Primary Examiner*—Richard L. Raymond
*Attorney, Agent, or Firm*—Daniel Reitenbach

[57] ABSTRACT

A compound of the formula

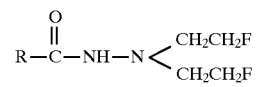

wherein R is a) phenyl; phenyl($C_1$–$C_4$ alkoxy); phenoxy; or benzyl; the phenyl ring of each substituent being optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, di($C_1$–$C_8$alkyl)amino, phenyl or phenoxy; or b) a 5- or 6-membered heterocyclic group comprising 1–3 heteroatoms selected from the group consisting of N, O or S, optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, or di-($C_1$–$C_8$alkyl)amino. These compounds and pesticidal compositions prepared therefrom, are useful as plant protecting agents for the control of insects, nematodes, and mites.

13 Claims, No Drawings

PESTICIDAL HYDRAZIDE DERIVATIVES

This is a division of application Ser. No. 08/614,291, filed Mar. 12, 1996, now U.S. Pat. No. 5,700,831.

FIELD OF THE INVENTION

This invention relates to novel hydrazide derivatives which exhibit activity as insecticides, acaricides and nematicides. This invention also relates to insecticidal, acaricidal or nematicidal compositions comprising the novel hydrazide derivatives as well as to methods of controlling insects, acarids and nematodes using the novel hydrazide derivatives.

BACKGROUND OF THE INVENTION

Destruction of field crops such as soybeans, corn, peanuts, cotton alfalfa, rice, and tobacco, by insects, acarids and nematodes presents a serious problem to agriculture. In addition, vegetables, such as tomatoes, potatoes, sugarbeet, carrots, peas, and the like, as well as fruits, nuts, ornamentals and seed bed crops such as apples, peaches, almonds, citrus fruit and grapes, are also vulnerable to such pests. Consequently, the development of new, more effective pesticides represents an ongoing scientific activity. More particularly, the development of pesticides which are effective as both ovicides and larvicides are of interest.

Chemical Abstracts 79:38541 and Chemical Abstracts 75:61807 describe certain N,N'-bis(2-chloroethyl)-hydrazides useful as antiblastic and antineoplastic agents.

SUMMARY OF THE INVENTION

A compound of the formula

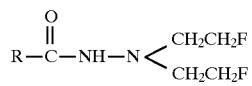

wherein R is a) phenyl; phenyl ($C_1$–$C_4$ alkoxy); phenoxy; or benzyl; the phenyl ring of each substituent being optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, di($C_1$–$C_8$alkyl)amino, phenyl or phenoxy; or b) a 5- or 6-membered heterocyclic group comprising 1–3 heteroatoms selected from the group consisting of N, O or S, the heterocyclic group being optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, or di($C_1$–$C_8$alkyl)amino. These compounds are useful as plant protecting agents for the control of insects and mites.

DETAILED DESCRIPTION OF THE INVENTION

Preferably, R is a) phenyl; phenyl ($C_1$–$C_4$ alkoxy); or phenoxy, the phenyl ring of each being optionally substituted with one or more of halogen, $C_1$–$C_4$ alkyl, $C_1$–$C_4$ alkoxy, $C_1$–$C_4$ haloalkyl, $C_1$–$C_4$ haloalkoxy, or di($C_1$–$C_4$ alkyl)amino, phenyl or phenoxy; or b) a 5- or 6-membered heterocyclic group comprising 1–3 heteroatoms selected from the group consisting of N, O or S, the heterocyclic group being optionally substituted with one or more of halogen, $C_1$–$C_4$ alkyl, $C_1$–$C_4$ alkoxy, $C_1$–$C_4$ haloalkyl, $C_1$–$C_4$ haloalkoxy, or di ($C_1$–$C_4$ alkyl) amino.

Preferred heterocyclic groups include optionally substituted furyl, thienyl, pyridinyl, pyrimidinyl, and thiazyl.

More preferably, R is a) phenyl optionally substituted with one or more of halogen, $C_1$–$C_4$ alkyl, $C_1$–$C_4$ haloalkoxy, or phenyl; or b) pyridinyl or thienyl, optionally substituted with one or more halogen or $C_1$–$C_4$ alkyl.

Useful R groups can include chloromethylphenyl, dichlorophenyl, ethoxyphenyl, chlorobromophenyl, nitrophenyl, methylbromophenyl, methylphenyl, fluorophenyl, dimethylaminophenyl, bromophenyl, phenoxyphenyl, chlorophenyl, methoxyphenyl, difluorophenyl, biphenyl, trifluoromethoxyphenylmethoxy, trimethylphenyl, trifluoromethylphenyl, dimethylphenyl, chlorobromophenyl, chloromethylthienyl, pyridinyl, and dimethoxyphenyl.

The compounds of this invention can be prepared by reacting a hydrazide of the formula $RCONHNH_2$, wherein R is as described above, with bromofluoroethane ($BrCH_2CH_2F$) and a base such as potassium hydroxide, sodium hydroxide, potassium carbonate or sodium carbonate.

The pesticidal compositions of this invention comprise (a) a compound of the formula

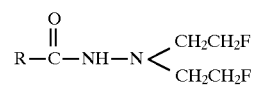

wherein R is as defined above,
and (b) a suitable carrier. Such suitable carriers can be solid or liquid in nature.

Suitable liquid carriers can include water, alcohols, ketones, phenols, toluene and xylenes. In such formulations, additives conventionally employed in the art can also be utilized, such as, for example, one or more surface active agents and/or inert diluents.

The pesticidal compositions can alternatively comprise solid carriers in the form of dusts, granules, wettable powders, pastes, aerosols, emulsions, emulsifiable concentrates, and water-soluble solids.

For example, the pesticidal compounds of this invention can be applied as dusts when admixed with or absorbed onto powdered solid carriers, such as mineral silicates, e.g., mica, talc, pyrophyllite and clays, together with a surface-active dispersing agent so that a wettable powder is obtained which can then be applied directly to the loci to be treated. Alternatively, the powdered solid carrier containing the compound admixed therewith can be dispersed in water to form a suspension for application in such form.

Granular formulations of the compounds, suitable for application by broadcasting, side dressing, soil incorporation or seed treatment, can be prepared using a granular or pelletized form of carrier such as granular clays, vermiculite, charcoal or corn cobs.

Alternatively, the pesticidal compounds can be applied as liquids or sprays when utilized in a liquid carrier, such as in a solution comprising a compatible solvent such as acetone, benzene, toluene or kerosene, or as dispersed in a suitable non-solvent medium, such as water.

Another method of application to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For pesticidal treatment of plants (such term including plant parts), the compounds of the present invention are preferably applied as aqueous emulsions containing a surface-active dispersing agent which can be non-ionic, cationic or anionic. Suitable surface-active agents have been described in the art, e.g., in U.S. Pat. No. 2,547,724 (columns 3 and 4). The compounds of the present invention can be mixed with such surface-active dispersing agents, with or without an organic solvent, as concentrates for the subsequent addition of water to yield aqueous suspensions of the compounds at desired concentration levels.

In addition, the compounds can be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/ formulation and the locus of treatment. Generally, however, concentrations of the compound as the active ingredient in pesticidally effective formulations can range from about 0.1 to about 95 percent by weight. Spray dilutions can be as low as a few parts per million, while at the opposite extreme, full strength concentrates of the compound can be usefully applied by ultra low volume techniques. Concentration per unit area, where plants constitute the loci of treatment, can range between about 0.01 and about 50 pounds per acre, with concentrations of between about 0.1 and about 10 pounds per acre preferably being employed for crops such as corn, tobacco, rice, and the like.

To combat pests, sprays of the compounds can be applied to the pests directly and/or to the plants upon which they feed or nest. The pesticidally active formulations can also be applied to the soil or other medium in which the pests are present.

The specific methods of application, as well as the selection and concentration of these compounds will, of course, vary depending upon such circumstances as geographic area, climate, topography, plant tolerance, etc. For specific circumstances, one skilled in the art can readily determine the proper compound, concentration and method of application by routine experimentation.

The compounds of the invention are particularly useful as insecticides, nematicides and acaricides, for foliar and/or soil application.

The following examples are provided to illustrate the present invention.

EXAMPLES

Example 1

Preparation of 4-chloro-2-methylbenzoic acid, 2,2-bis(2-fluoroethyl)hydrazide (Compound No. 1)

To 50 mL of ethanol was added 5 gm of 4-chloro-2-methylbenzhydrazide followed by 4 gm of sodium hydroxide pellets. After stirring for 15 min, 7.5 gm of 1-bromo-2-fluoroethane was added dropwise. After this addition was complete, the resulting mixture was stirred for 4 hours, then diluted with 100 mL of water, and, finally, extracted with ethyl acetate. Upon evaporation of the solvent, an oil remained which was purified by chromatography, to produce 1.7 g of 4-chloro-2-methyl-benzoic acid, 2,2-bis(2-fluoroethyl)hydrazide as an off white solid, mp 85°–87° C.

The compounds summarized in Table 1 were prepared using an analogous procedure. Each of the compounds is characterized by its NMR data.

TABLE I

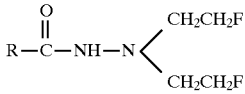

| NO. | R | NMR DATA (PPM) in DMSO |
|---|---|---|
| 1 | 2-CH$_3$,4-ClC$_6$H$_3$ | S(3) 2.3; t(2) 3.0; t(2) 3.4; t(2) 4.2; t(2) 5.0; S(3) 7.3; S(1) 9.5 |
| 2 | 2,4-ClC$_6$H$_3$ | t(2) 3.0; t(2) 3.4; t(2) 4.2; t(2) 5.0; m(3) 7.1–7.5; S(1)9.5 |
| 3 | 4-OC$_2$H$_6$C$_6$H$_4$ | t(3) 1.4; t(2) 3.1; t(2) 3.5; m(4) 3.8–4.3; t(2) 5.0; d(2)6.9; d(2) 7.6 |
| 4 | 2-Cl,4-BrC$_6$H$_3$ | S(1) 9.5; t(2) 3.0; t(2) 3.5; t(2) 4.2; t(2) 5.0; m(3) 7.4–7.8; 3(1) 9.7 |
| 5 | 4-NO$_2$C$_6$H$_4$ | t(2) 3.0; t(2) 3.4; t(2).4.2; t(2) 5.0; S(4) 7.7; S(1) 9.6 |
| 6 | C$_6$H$_5$ | t(2) 3.1; t(2) 3.5; t(2) 4.1; t(2) 5.0; m(5) 7.4–7.9; S(1) 9.7 |
| 7 | 2-CH$_3$,4-BrC$_6$H$_3$ | S(3) 2.3; t(2) 3.1; t(2) 3.5; t(2) 4.2; t(2) 5.0; S(3) 7.3; S(1) 9.5 |
| 8 | 2-CH$_3$C$_6$H$_4$ | S(3) 2.3; t(2) 3.0; t(2) 3.5; t(2) 4.3; t(2) 5.0; S(4) 7.3; S(1) 9.5 |
| 9 | 2-NO$_2$C$_6$H$_4$ | t(2) 3.0; t(2) 3.5; t(2) 4.2; t(2) 5.0; m(4) 7.5–8.0; S(1) 9.5 |
| 10 | 2-FC$_6$H$_4$ | t(2) 3.0; t(2) 3.4; t(2) 4.2; t(2) 5.0; m(4) 7.3–7.7; S(1) 9.5 |
| 11 | 4-N(CH$_3$)$_2$C$_6$H$_4$ | S(6) 2.8; t(2) 3.0; t(2) 3.4; t(2) 4.2; t(2) 4.2; t(2) 5.0; S(4) 7.4; S(1) 9.6 |
| 12 | 4-BrC$_6$H$_4$ | t(2) 3.0; t(2) 3.3; t(2) 4.3; t(2) 5.0; S(4) 7.5; S(1)9.5 |
| 13 | 3-OC$_6$H$_5$C$_6$H$_4$ | t(2) 3.0; t(2) 3.4; t(2) 4.2; t(2) 5.0; m(9) 7.1–7.7; S(1) 9.5 |
| 14 | 4-ClC$_6$H$_4$ | t(2) 3.0; t(2) 3.4; t(2) 5.0; S(4)7.5; S(1) 9.5 |
| 15 | 2-OC$_6$H$_5$C$_6$H$_4$ | t(2) 3.0; t(2) 3.4; t(2) 4.2; t(2) 5.0; m(9) 7.1–7.7; S(1) 9.6 |
| 16 | 2-OCH$_3$C$_6$H$_4$ | t(2) 3.0; t(2) 3.4; S(3) 3.9; t(2) 4.2; t(2) 5.0; m(4) 7.0–7.3; S(1) 9.5 |
| 17 | 2,6-FC$_6$H$_3$ | t(2) 3.0; t(2) 3.4; t(2) 4.2; t(2) 5.0; m(3) 7.3–7.7; S(1) 9.6 |
| 18 | 2-C$_6$H$_5$C$_6$H$_4$ | t(2) 3.0; t(2) 3.4; t(2) 4.3; t(2) 5.0; m(9) 7.3–7.7; 5(1) 9.5 |
| 19 | 4-C$_6$H$_5$C$_6$H$_4$ | t(2) 3.0; t(2) 3.4; t(2) 4.2; t(2) 5.0; m(9) 7.3–7.7; S(1)9.5 |
| 20 | 4-OCF$_3$C$_6$H$_4$OCH$_2$ | t(2) 3.0; t(2) 3.4; t(2) 4.2; S(2) 4.5; t(2) 4.9; m(4) 6.9–7.3; S(1) 9.5 |
| 21 | 2,4,6-CH$_3$C$_6$H$_2$ | S(9) 2.3; t(2) 3.0; t(2) 3.4; t(2) 4.2; t(2) 5.0; m(2) 7.3–7.5; S(1) 9.5 |
| 22 | 4-OCH$_3$C$_6$H$_4$ | t(2) 3.0; t(2) 3.4; S(3) 3.9; t(2) 4.2; t(2) 5.0; S(4) 7.2; S(1) 9.5 |
| 23 | 4-CF$_3$C$_6$H$_4$ | t(2) 3.0; t(2) 3.4; t(2) 4.2; t(2) 5.0; S(4) 7.3; S(1) 9.5 |
| 24 | 4-CH$_3$C$_6$H$_4$ | S(3) 2.3; t(2) 3.0; t(2) 3.4; t(2) 4.2; t(2) 5.0; S(4) 7.3; S(1) 9.5 |
| 25 | 3-CH$_3$C$_6$H$_4$ | S(3) 2.2; t(2) 3.0; t(2) 3.4; t(2) 4.2; t(2) 5.0; S(4) 7.3; S(1) 9.6 |
| 26 | 4-OCF$_3$C$_6$H$_4$ | t(2) 3.0; t(2) 3.4; t(2) 4.2; t(2) 5.0; S(4) 7.3; S(1) 9.7 |
| 27 | 2,4-FC$_6$H$_3$ | t(2) 3.0; t(2) 3.4; t(2) 5.0; m(3) 7.2–7.6; S(1) 9.5 |
| 28 | 3,5-ClC$_6$H$_3$ | t(2) 3.0; t(2) 3.4; t(2) 4.2; t(2) 5.0; m(3) 7.2–7.6; S(1)9.5 |
| 29 | 3-Cl,4-CH$_3$C$_6$H$_3$ | S(3) 2.4; t(2) 3.0; t(2) 3.4; t(2) 4.2; t(2) 5.0; S(1) 6.9; S(1) 9.5 |
| 30 | 2,4-CH$_3$C$_6$H$_3$ | S(6) 2.3; t(2) 3.0; t(2) 3.4; t(2) 4.2; t(2) 5.0; m(3) 7.2–7.6; S(1) 9.5 |
| 31 | 3-Cl,4-BrC$_6$H$_3$ | t(2) 3.0; t(2) 3.0; t(2) 3.4; t(2) 4.2; t(2) 5.0; S(3) 7.3; S(1) 9.5 |
| 32 | 2,5-OCH$_3$C$_6$H$_3$ | t(2) 3.0; t(2) 3.4; S(6) 3.8; t(2) 4.2; t(7.3–7.8)3; S(1) 9.5 |
| 33 | 2,5-ClC$_6$H$_3$ | t(2) 3.0; t(2) 3.4; t(2) 4.2; t(2) 5.0; S(3) 7.4; S(1) 9.5 |
| 34 | 3-Cl,4-CH$_3$-2-C$_4$HS | s(3) 2.1; t(2) 3.0; t(2) 3.4; t(2) 4.2; t(2) 5.0; s(1) 7.5; s(1) 9.5 |
| 35 | 3-C$_5$H$_4$N | t(2) 3.0; t(2) 3.4; t(2) 4.1; t(2) 5.0; m(4) 7.4–9.0; s(1) 10.0 |

Example 2

Stock Solution Preparation

Stock solutions for the compounds to be tested were prepared at 3000 parts per million (ppm) by dissolving 0.3 gram of each compound to be tested in 10 ml of acetone and adding 90 ml of distilled water plus 4 drops of ethoxylated sorbitan monolaurate, a wetting agent. This stock solution was used in the remaining examples demonstrating the pesticidal use of representative compounds of this invention. For each example that follows, the stock solution was used and the specified dilutions made. All the tests discussed below, which involved treatment with compounds of this invention, were always repeated with controls, in which no active compound was present, for use as a comparison for calculating the percent control of the tested compound.

Example 3

Rice Planthopper Foliar Test

The stock solution (3000 ppm) prepared in Example 2 for each compound tested was diluted to 1000 ppm (test solution). Using a spray atomizer, each test solution was sprayed onto a separate pot containing approximately 20 Mars variety rice seedlings. One day after spraying, the plants were covered with a tubular cage and twenty adult rice delphacides, *Sogatodes orizicola*, were transferred into each cage. Five days after transferring, counts were made of the surviving planthoppers in each pot and percent control was estimated.

Results of the rice planthopper (RHP) are presented in Table 2 below.

Example 4

Southern Corn Rootworm Test

The stock solution (3000 ppm) prepared in Example 2 for each compound tested was diluted to 100 ppm (test solution). 2.5 ml of each test solution was pipetted onto a filter paper (Whatman #3) at the bottom of a 100 mm petri dish. Two corn seedlings were soaked in a test solution for 1 hour and then transferred to the petri dish containing the same test solution. After 24 hours, each dish was loaded with 5 second instar larvae of the southern corn rootworm, *Diabrotica undecimpunctata*. After five days, the number of live larvae were determined and the percent control, corrected by Abbott's formula (see J. Economic Entomology, 18, 265–267 (1925)), was calculated.

The results of the testing of corn rootworm (CR) are given in Table 2 below.

Example 5

Tobacco Budworm Test

The undiluted stock solution (3000 ppm) (test solution) prepared in Example 2 for each compound was used for this test. 0.2 ml of each test solution was pipetted onto the surface of each of 5 diet cells, allowed to spread over the surfaces and air dried for two hours. Then a second instar larva of *Heliothis virescens* was introduced into each cell. After 14 days, the number of living larvae was determined for each test solution and percent control, corrected by Abbott's formula, was calculated.

The results of the testing of tobacco budworms (TB) are given in Table 2 below.

Example 6

Mite Adulticide and Mite Ovicide/Larvicide Tests

The stock solution (3000 ppm) prepared in Example 2 for each compound tested was diluted to 1000 ppm (test solution).

One day before treatment, a "Figure 8" configuration of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when they were removed. Each plant was then sprayed to run off with one of the test solutions.

One day following treatment, groups of approximately 25 adult mites were transferred into the adulticide rings. Five days later these rings were examined for live mites remaining on the leaves. The percent control was estimated based on the number of mites surviving on the check plants.

Nine days following treatment the ovicide/larvicide rings were examined for hatched eggs and living immature mites. The percent control was estimated based on the number of eggs hatching and immature mites surviving on the check plants. When the treatment effect was to eggs, control was designated as ovicidal (O); when the treatment effect was to immatures, control was designated as larvicidal (L).

Results of the mite adulticide (MI) and ovicide/larvicide (MIOLV) tests are presented in Table 2 below.

Example 7

Nematode Test

The stock solution (3000 ppm) prepared in Example 2 was diluted to 1000 ppm (test solution). For each test solution, 25 ml was drenched onto separate 500 grams of soil infested with root knot nematode (*Meloidogyne incognita*) eggs in a pot, for a soil concentration of 50 ppm sc.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table 2 below.

| Cmpd. No. | RPH | CR | TB | MI | MIOVL | NE |
|---|---|---|---|---|---|---|
| 1 | 100 | 0 | 20 | 100 | 75(O) | 0 |
| 2 | 100 | 25 | 33 | 90 | 100(O) | 0 |
| 3 | 100 | 0 | 0 | 0 | 0 | 0 |
| 4 | 100 | 0 | 37 | 0 | 50(O) | PT |
| 5 | 94 | — | — | — | — | — |
| 6 | 95 | 0 | 0 | 50 | 0 | 100 |
| 7 | 100 | 0 | 20 | 50 | 50(O) | 0 |
| 8 | 100 | 0 | 20 | 70 | 70(O) | PT |
| 9 | 95 | 0 | 0 | 30 | 30(O) | PT |
| 10 | 100 | 0 | 20 | 0 | 70(O) | 0 |
| 11 | 100 | 0 | 0 | 0 | 0 | 0 |
| 12 | 100 | 20 | 75 | 0 | 60(O) | 80 |
| 13 | 100 | 0 | 0 | 0 | 0 | 70 |

-continued

| Cmpd. No. | Percent Control | | | | | |
|---|---|---|---|---|---|---|
| | RPH | CR | TB | MI | MIOVL | NE |
| 14 | 100 | 0 | 0 | 0 | 50(0) | 0 |
| 15 | 100 | 20 | 0 | 0 | 50(0) | 0 |
| 16 | 75 | 0 | 0 | 0 | 30(0) | 0 |
| 17 | 100 | 20 | 0 | 100 | 100(0) | 0 |
| 18 | 100 | 16 | 0 | 99 | 70(0) | 50 |
| 19 | 80 | 37 | 80 | 0 | 0 | 0 |
| 20 | 100 | 37 | 0 | 90 | 70(0) | PT |
| 21 | 100 | 100 | 20 | 0 | 0 | 70 |
| 22 | 100 | 0 | 0 | 0 | 70(0) | 70 |
| 23 | 75 | 0 | 0 | 0 | 0 | 0 |
| 24 | 80 | 0 | 0 | 0 | 100(0) | 0 |
| 25 | 100 | 20 | 0 | 75 | 100(0) | 0 |
| 26 | 100 | 47 | 40 | 100 | 100(0) | 0 |
| 27 | 90 | 0 | 60 | 20 | 100(0) | 0 |
| 28 | 100 | 0 | 40 | 90 | 100(0) | 100 |
| 29 | 100 | 0 | 40 | 0 | 100(0) | 0 |
| 30 | 100 | 0 | 0 | 0 | 70(0) | 100 |
| 31 | 100 | 0 | 40 | 90 | 100(0) | 100 |
| 32 | 100 | 0 | 0 | 90 | 100(0) | 0 |
| 33 | 100 | 0 | 0 | 0 | 0 | 0 |
| 34 | 100 | 0 | 40 | 0 | 100(0) | 0 |
| 35 | 100 | 0 | 0 | 98 | 50(0) | PT |

*Tested at 500 ppm
— Not tested
PT Phytotoxic to host plant

Example 8

Rice Planthopper Systemic Test 200 ppm test solutions of the compounds were prepared by dissolving 0.01 gram of each compound to be tested in 5 ml of acetone and adding 45 ml of distilled water plus 2 drops of ethoxylated sorbitan monolaurate.

Each of a series of pots held about 475 grams of moist soil and contained approximately 20 Mars variety rice seedlings, 8 days old from seed. A 25 ml aliquot of each test solution was injected into the root zone of a separate pot with a hypodermic needle and syringe. The resulting soil concentration of each compound tested was 10 ppmsc (parts per million soil concentration).

One day after treatment, the plants were covered with a tubular cage and ten adult rice delphacids, *Sogatodes orizicola*, were transferred into each cage. Five days after transferring, counts were made of the surviving planthoppers in each pot and the adjusted percent control was calculated using Abbotts formula.

The results of this test of rice planthoppers (RPH) are given in Table 3 below.

TABLE 3

| Compound No. | Adjusted Percent Control RPH |
|---|---|
| 1 | 100 |
| 4 | 100 |
| 6 | 100 |
| 9 | 100 |
| 10 | 100 |
| 11 | 100 |
| 12 | 100 |
| 17 | 100 |
| 18 | 100 |
| 19 | 100 |
| 22 | 100 |
| 24 | 100 |

TABLE 3-continued

| Compound No. | Adjusted Percent Control RPH |
|---|---|
| 30 | 100 |
| 33 | 100 |

Example 9

Aphid Foliar Test

The stock solution (3000 ppm) prepared in Example 2 for each compound tested was diluted to 500 ppm (test solution). Using a spray atomizer, each test solution was sprayed onto separate tomato plants infested with green peach aphid (GPA) *Myzus persicae*. Percent control was estimated at six days post treatment. The results of this test are presented in Table 4 below.

TABLE 4

| Compound No. | Estimated Percent Control GPA |
|---|---|
| 1 | 100 |
| 3 | 100 |
| 4 | 100 |
| 6 | 100 |
| 9 | 100 |

What is claimed is:

1. A compound of the formula

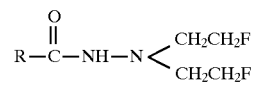

wherein R is pyridinyl or thienyl, optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, or di($C_1$–$C_8$ alkyl) amino.

2. A compound as recited in claim 1 wherein R is pyridinyl or thienyl, optionally substituted with one or more of halogen, $C_1$–$C_4$ alkyl, $C_1$–$C_4$ alkoxy, $C_1$–$C_4$ haloalkyl, $C_1$–$C_4$ haloalkoxy, or di-($C_1$–$C_4$ alkyl)amino.

3. A compound as recited in claim 2 wherein R is pyridinyl or thienyl, optionally substituted by halogen or $C_1$–$C_4$ alkyl.

4. A compound as recited in claim 2 wherein R is chloromethylthienyl or pyridinyl.

5. A pesticidal composition comprising
   A) a pesticidally effective amount of a compound as recited in claim 1; and
   B) an acceptable carrier.

6. A pesticidal composition comprising
   A) a pesticidally effective amount of a compound as recited in claim 2; and
   B) an acceptable carrier.

7. A pesticidal composition comprising
   A) a pesticidally effective amount of a compound as recited in claim 3; and
   B) an acceptable carrier.

8. A pesticidal composition comprising
   A) a pesticidally effective amount of a compound as recited in claim 4; and
   B) an acceptable carrier.

9. A process for controlling undesirable pests which comprises applying to a locus to be protected a pesticidally effective amount of a compound of the formula

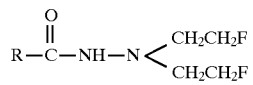

wherein R is a 5- or 6-membered heterocyclic group comprising 1–3 heteroatoms selected from the group consisting of N, O or S, the heterocyclic group being optionally substituted with one or more of halogen, nitro, $C_1$–$C_8$ alkyl, $C_1$–$C_8$ alkoxy, $C_1$–$C_8$ haloalkyl, $C_1$–$C_8$ haloalkoxy, or di($C_1$–$C_8$ alkyl)amino.

10. A process for controlling undesirable pests as recited in claim 9 wherein R is a 5- or 6-membered heterocyclic group comprising 1–3 heteroatoms selected from the group consisting of N, O or S, optionally substituted with one or more of halogen, $C_1$–$C_4$ alkyl, $C_1$–$C_4$ alkoxy, $C_1$–$C_4$ haloalkyl, $C_1$–$C_4$ haloalkoxy or di-($C_1$–$C_4$ alkyl)amino.

11. A process for controlling undesirable pests as recited in claim 10 wherein the 5- or 6-membered heterocyclic group is furyl, thienyl, pyridinyl, pyrimidinyl, or thiazyl.

12. A process for controlling undesirable pests which comprises applying to a locus to be protected a pesticidally effective amount of a compound in accordance with claim 3.

13. A process for controlling undesirable pests which comprises applying to a locus to be protected a pesticidally effective amount of a compound in accordance with claim 4.

* * * * *